US00PP29806P3

(12) United States Plant Patent
Smith

(10) Patent No.: US PP29,806 P3
(45) Date of Patent: Nov. 6, 2018

(54) ***CHRYSANTHEMUM* PLANT NAMED 'CIFZ0053'**

(50) Latin Name: *Chrysanthemum x morifolium*
Varietal Denomination: CIFZ0053

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/530,501

(22) Filed: Jan. 23, 2017

(65) Prior Publication Data

US 2018/0213704 P1 Jul. 26, 2018

(51) Int. Cl.
*A01H 5/02* (2018.01)
*A01H 6/14* (2018.01)

(52) U.S. Cl.
USPC ..... Plt./293
CPC ..... *A01H 6/1424* (2018.05)

(58) Field of Classification Search
USPC ..... Plt./293, 287, 290
CPC ..... A01H 5/0255; A01H 5/025; A01H 5/02; A01H 5/00; A01H 6/1424
See application file for complete search history.

*Primary Examiner* — June Hwu
(74) *Attorney, Agent, or Firm* — Dale Skalla

(57) ABSTRACT

A new garden type *Chrysanthemum* plant named 'CIFZ0053' particularly distinguished by the small size red-bronze decorative flower, large size plant with round sphere plant habit and a natural season response in mid-late October.

1 Drawing Sheet

Latin name of the genus and species of the plant claimed: *Chrysanthemum* x *morifolium.*

Varietal denomination: 'CIFZ0053'.

BACKGROUND OF THE NEW PLANT

The present invention comprises a new *Chrysanthemum*, botanically known as *Chrysanthemum* x *morifolium*, and hereinafter referred to by the variety name 'CIFZ0053'.

'CIFZ0053' is a product of a planned breeding program. The new cultivar has small size red-bronze decorative flower, large size plant with round sphere plant habit and a natural season response in mid-late October.

'CIFZ0053' originated from a mutation: Stock x-rayed at 1750 RAD in October of 2013. Single cutting sport from the stock.

The female parent was the unnamed lavender/pink colored seedling from own breeding '11-M262'.

When compared to the female parent, 'CIFZ0053' has:

1) Similar flower type and size but red-bronze not dark lavender/pink color like the sport parent
2) Blackcloth and natural season response is a day or two slower than the sport parent
3) Similar plant habit and slightly larger plant size than the sport parent No male parent.

The first act of asexual reproduction of 'CIFZ0053' was accomplished when vegetative stem tip cuttings were propagated from the initial selection. This initial selection took place on Apr. 16, 2014 in Gilroy, Calif.

BRIEF SUMMARY OF INVENTION

Horticultural examination of plants grown from cuttings of the plant initiated in May 2014 in Gilroy, Calif., and continuing thereafter, has demonstrated that the combination of characteristics as herein disclosed for 'CIFZ0053' are firmly fixed and are retained through successive generations of asexual reproduction.

'CIFZ0053' has not been observed under all possible environmental conditions. The phenotype may vary significantly with variations in environment such as temperature, light intensity and day length.

A Plant Breeder's Right for this cultivar was applied for in the European Union on Nov. 22, 2016, No. 2016/2883. 'CIFZ0053' has not been made publicly available prior to the effective filing date of this application, notwithstanding any disclosure that may have been made less than one year prior to the effective filing date of this application by the inventor or another who obtained 'CIFZ0053' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0053' with colors being as true as possible with an illustration of this type.

Figure 1:
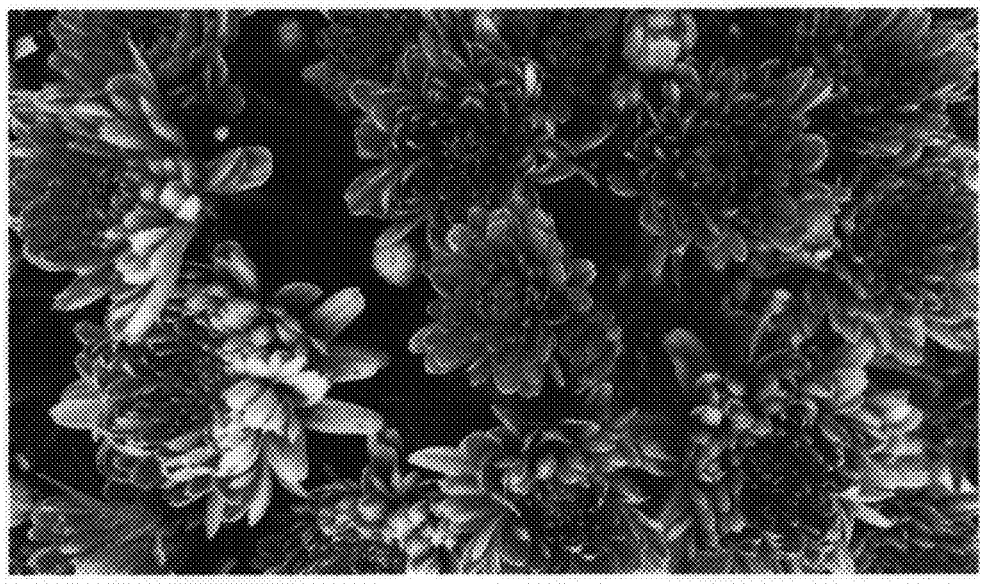
Figure 2:
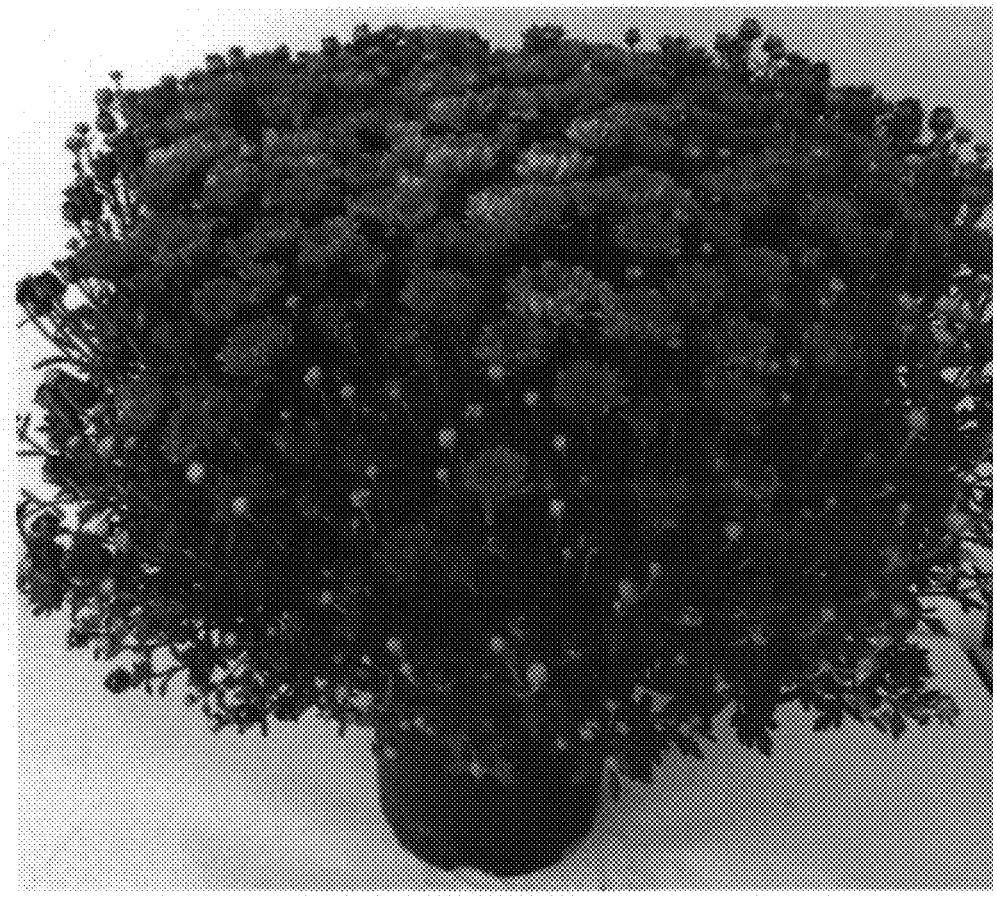

The photographic drawings show in FIG. 1 a close view of flower of the new variety and in FIG. 2 a flowering plant from an outdoor trial.

The aforementioned photographs: FIG. 1, as well as FIG. 2, were taken in October 2016 both showing a plant from the same natural outdoor trial in Gilroy, Calif. These plants were about 18 weeks of age. One rooted cutting per pot had been planted in a one gallon pot, not pinched in week 22. Plants started flowering end of September.

DETAILED BOTANICAL DESCRIPTION

The measurements were taken in Gilroy, Calif. in October 2016 on the plants from the aforementioned trial.

Color references are made to The Royal Horticultural Society Colour Chart (R.H.S.) 2001.

TABLE 1

DIFFERENCES BETWEEN THE NEW VARIETY 'CIFZ0053' AND 'Brunette Yobarbie':

| | 'CIFZ0053' | 'Brunette Yobarbie', U.S. Plant Pat. No. 21,322 |
|---|---|---|
| Flowering response (blackcloth): | 1 week slower | 1 week faster |
| Flowering response (natural): | 0.5 week slower | 0.5 week faster |
| Flower size: | Bit smaller flower | Bit bigger flower |
| Plant habit or size: | Larger plant with more spread and therefore rounder habit especially in blackcloth compared to 'Brunette Yobarbie' | Smaller plant with more oval habit especially in black-cloth compared to 'CIFZ0053' |

TABLE 2

DIFFERENCES BETWEEN THE NEW VARIETY 'CIFZ0053' 'Staviski Red':

| | 'CIFZ0053' | 'Staviski Red', Not patented |
|---|---|---|
| Flowering response (blackcloth): | 1 week slower | 1 week faster |
| Flowering response (natural): | Similar | Similar |
| Frost tolerance | Frost tolerant | Not frost tolerant |
| Flower shape: | Less disc florets | More disc florets |
| Plant habit or size: | Larger plant size | Smaller plant size |

Plant:

*Form, growth and habit.*—Herbaceous garden-type, stems upright and outwardly spreading, freely branching, strong and moderately vigorous growth habit.

*Plant height (above soil).*—16-20 cm.

*Plant height (inflorescence included).*—19-23 cm.

*Plant width.*—42-46 cm.

Roots:

*Number of days to initiate roots.*—About 4-6 days at about 22 degrees C.

*Number of days to produce a rooted cutting.*—14-16 days at 22 degrees C.

*Type.*—Fine, fibrous, free branching.

*Color.*—RHS N155B but whiter.

Foliage:

*Arrangement.*—Alternate.

*Immature leaf, color upper surface.*—Between RHS 136A and RHS 136B.

*Immature leaf, color lower surface.*—RHS 137B.

*Mature leaf, color, upper surface.*—RHS 139A.

*Mature leaf, color lower surface.*—RHS 137B.

*Length.*—3.5-3.9 cm.

*Width.*—2.0-2.7 cm.

*Shape.*—Ovate.

*Base shape.*—Attenuate.

*Apex shape.*—Acute.

*Margin.*—3 main lobes, iregularly serrulate.

*Texture, upper surface.*—Bifid hairs.

*Texture, lower surface.*—Bifid hairs.

*Color of veins, upper surface.*—RHS 139B.

*Color of veins, lower surface.*—RHS 137D.

*Pattern of veining.*—Palmate.

*Petiole color.*—RHS 139C.

*Petiole length.*—1.0-1.6 cm.

*Diameter.*—0.1-0.2 cm.

*Texture.*—Covered with bifid hairs.

Stem:

*Quantity of main branches per plant.*—13-15.

*Color of stem.*—RHS 138B.

*Length of stem.*—10.5-15 cm.

*Diameter.*—0.3-0.6 cm.

*Length of internodes.*—1.0-2.0 cm.

*Texture.*—Bifid hairs.

*Color of peduncle.*—RHS 138A.

*Length of peduncle.*—8.5-13 cm.

*Peduncle diameter.*—0.15 cm.

*Texture.*—Covered with bifid hairs.

Inflorescence:

*Type.*—Compositae, solitary, decorative-type inflorescences borne terminally above foliage.

*Quantity of short days to flowering (response time).*—Approximately 7 weeks.

*Natural season flowering.*—Mid-late October.

*Quantity of inflorescences per plant.*—200-250 buds.

*Lastingness of individual blooms on the plant.*—About six weeks from first color, depending on conditions.

*Fragrance.*—Slightly spicy.

Bud (when showing color):

*Color.*—Between RHS 59A and RHS 59B.

*Length.*—1.1-1.3 cm.

*Width.*—0.8-1.0 cm.

*Shape.*—Oblate (almost globular).

Immature inflorescence:

*Diameter.*—1.8-2.3 cm.

*Color of ray florets, upper surface.*—Closest to RHS 181A, RHS 14C at base.

*Color of ray florets, lower surface.*—RHS 181A, overlain with RHS 155B; RHS 14C at base.

Mature inflorescence:

*Diameter.*—3.0-3.5 cm.

*Depth.*—1.5-1.8 cm.

*Total diameter of disc.*—None Present.

*Receptacle color.*—RHS 145B.

*Receptacle height.*—0.4 cm.

*Receptacle diameter.*—0.6-1.1 cm.

Ray florets:

*Average quantity of florets.*—Between 100 and 130 in many whorls.

*Color of florets, upper surface.*—Between RHS 181A and RHS 181B, RHS 10A at base.

*Color inner surface.*—RHS 181A overlain with RHS 155B, RHS 10A at base.

*Length.*—0.8-1.2 cm.

*Width/diameter.*—0.35-0.4.

*Shape.*—Oblong to elliptical.

*Apex shape.*—Most often emarginated or praemorse.

*Base shape.*—Attenuate.

*Margin.*—Entire.

*Texture, upper surface.*—Smooth.

*Lower surface.*—Smooth.

Disc florets: None present.

Phyllaries:

*Quantity.*—70.

*Color, upper surface.*—RHS 136A to RHS 136B.

*Color, lower surface.*—RHS 137B.

*Length.*—0.7-0.8 cm.

*Width*.—0.15-0.2 cm.
*Shape*.—Lanceolate.
*Apex shape*.—Acute.
*Base*.—Fused.
*Margins*.—Entire, some with papery edges.
*Texture, upper surface*.—Glabrous.
*Texture, lower surface*.—Bifid hairs.

Reproductive organs:

*Pistil*.—One.
*Length*.—0.5 cm.
*Style color*.—RHS 1C.
*Style length*.—0.35-0.4 cm.
*Stigma color*.—RHS 7D.
*Stigma shape*.—Bi-lobed.
*Ovary color*.—RHS 145C.
*Ovary length*.—0.15 cm.
*Ovary width*.—0.1 cm.

Androecium:

*Stamens*.—None, as they are usually present in disc florets only, which are not developed.
*Fertility/seed set*.—Has not been determined to date.
*Disease/pest resistance*.—Has not been determined to date.
*Cold hardiness*.—Frost Tolerant.

What is claimed is:

1. A new and distinct variety of *Chrysanthemum* plant named 'CIFZ0053' substantially as illustrated and described herein.

* * * * *